(12) United States Patent
Sauer (10) Patent No.: US 6,921,408 B2
(45) Date of Patent: Jul. 26, 2005

(54) APPARATUS FOR SEWING TISSUE AND METHOD OF USE

(75) Inventor: Jude S. Sauer, Pittsford, NY (US)

(73) Assignee: LSI Solutions, Inc., Victor, NY (US)

( * ) Notice: Subject to any disclaimer, the term of this patent is extended or adjusted under 35 U.S.C. 154(b) by 439 days.

(21) Appl. No.: 10/095,383

(22) Filed: Mar. 12, 2002

(65) Prior Publication Data

US 2003/0176874 A1 Sep. 18, 2003

(51) Int. Cl.$^7$ .............................................. A61B 17/12

(52) U.S. Cl. ...................................... 606/144; 606/139

(58) Field of Search ........................... 606/1, 138, 139, 606/144, 148, 222–233

(56) References Cited

U.S. PATENT DOCUMENTS

| | | | |
|---|---|---|---|
| 5,318,577 A | * | 6/1994 | Li .............................. 606/147 |
| 5,391,173 A | | 2/1995 | Wilk |
| 5,409,453 A | | 4/1995 | Lundquist et al. |
| 5,431,666 A | | 7/1995 | Sauer et al. |
| 5,507,757 A | | 4/1996 | Sauer et al. |
| 5,520,702 A | | 5/1996 | Sauer et al. |
| 5,562,686 A | | 10/1996 | Sauer et al. |
| 5,626,588 A | | 5/1997 | Sauer et al. |
| 5,626,590 A | | 5/1997 | Wilk |
| 5,643,289 A | | 7/1997 | Sauer et al. |
| 5,669,917 A | | 9/1997 | Sauer et al. |
| 5,713,908 A | * | 2/1998 | Jameel et al. ............... 606/148 |
| 5,766,183 A | | 6/1998 | Sauer |
| 5,908,428 A | * | 6/1999 | Scirica et al. ............... 606/139 |
| 5,948,001 A | | 9/1999 | Larsen |
| 6,319,272 B1 | | 11/2001 | Brenneman et al. |

OTHER PUBLICATIONS

Brochure entitled "Sew–Right SR 5, The Single Squeeze Suturing Device", LSI Solutions, Copyright 2000.
Brochure entitled "Ti–KNOT TK 5, The Device to Instantly Secure and Trim Suture", LSI Solutions, Copyright 2000.

* cited by examiner

Primary Examiner—Glenn K. Dawson
(74) Attorney, Agent, or Firm—Kenneth J. Lukacher (57) ABSTRACT

An apparatus for sewing tissue especially useful for tissue ligation, is provided having a housing and a hollow shaft which extends from the housing. At the distal end of the shaft along its interior is a movable driver member disposed opposite a fixed member. A needle is pivotably mounted at one end to the driver member to extend, when the driver member is moved forward, through a slot in the fixed member and an opening in the shaft, and to retract back into the shaft when the driver member is moved backward. At the distal end of needle is a slotted hook for capturing a loop of suture. The free ends of the loop of suture extend through a hole of the fixed member. A lever pivotably mounted in the housing is coupled to the driver member to translate linear motion forwards or backwards to the driver member. In a method for sewing tissue, the needle is driven forward to extend from the apparatus and then through tissue adjacent tissue to be sewn. The loop of suture is then removed from the needle prior to its retraction leaving the loop of suture extending through the tissue. The apparatus is repositioned with the needle on the opposite side of the tissue to be sewn. The loop of suture is captured again on the needle, and then the needle is retracted with the loop of suture into the apparatus. While holding one end of the suture, the apparatus is removed and one side of the loop of suture is drawn through and around the tissue to be sewn. The mid section of the suture is thus behind the tissue and the suture ends on opposite sides of the tissue are available to facilitate securing or tying of the suture to close a wound or to ligate a tissue structure.

26 Claims, 8 Drawing Sheets

APPARATUS FOR SEWING TISSUE AND METHOD OF USE

FIELD OF THE INVENTION

The present invention relates to an apparatus and method for sewing tissue, and particularly to an apparatus and method for applying suture through tissue, such as to close a wound or ligate a tissue structure. The invention is useful to provide a surgical instrument for sewing tissue during laproscopic surgery.

BACKGROUND OF THE INVENTION

Laproscopic surgery involves the use of instruments through small incisions in the patient, avoiding the need for traditional open surgery which is both invasive to the patient and can lead to long patient recovery time. Often due to space constraints within the body of the patient, these instruments must have specialized distal ends to enable the various steps of the procedure. One such step often required is ligating or binding of tissue, such as a vein, or for closing a wound, such as at a surgical resection site. For example, during prostatectomy, the full or partial removal of the prostate gland, the dorsal vein of the penis in front of the urethra of the male patient often must be ligated, e.g., bound or tied with suture, to minimize potential bleeding from the vascular complex. However, the space about the dorsal vein complex, the angle of entry of instruments, and a preference to use very small diameter instruments make ligating this complex difficult. Thus, a specialized instrument is needed which can be laproscopically inserted into a patient and operated in a small space where traditional surgical instruments are not practical.

SUMMARY OF THE INVENTION

Accordingly, it is an object of the present invention to provide an improved apparatus and method for sewing tissue which can be used in laproscopic surgical procedures.

It is another object of the present invention to provide an improved apparatus and method for sewing tissue using a needle which can be selectively extended from the distal end of the apparatus to place suture about tissue, such as to close a wound or ligate tissue.

Briefly described, the present invention embodies an apparatus having a housing, a hollow shaft which extends from the housing. At the distal end of the shaft along its interior is a movable driver member disposed opposite a fixed member. The fixed member may be provided by a cap received into the shaft at the distal end. A needle is provided having one end pivotably mounted to the driver member to extend, when the driver member is moved forward, through a slot in the fixed member and an opening in the shaft. At the other distal end of the needle is the needle's tip and a hook (or slot) capable of retaining a loop of suture material. The free ends of the loop of suture material extend through a hole in the fixed member. The needle is shaped to curve towards the opening in the shaft through the slot so as to facilitate its exiting the shaft. A guide member or pin is provided in the slot to guide the needle through the opening when driven forward, and/or the needle slides along the lower part of the slot in the fixed member. A lever pivotably mounted in the housing is coupled to the driver member to translate linear motion forward or backward to the driver member, and thereby control the extension and retraction of the needle at the distal end of the apparatus.

A method for sewing tissue using the apparatus is also provided with the apparatus loaded with a loop of suture material upon the needle's hook by the steps of: placing the distal end of the apparatus such that the opening of the shaft and slot of the fixed member is disposed near the tissue adjacent the tissue to be sewn, driving the needle forward through the opening of the shaft to extend the needle, passing the needle and loop of suture material through the adjacent tissue along one side of the tissue to be sewn, removing the loop of suture material from the needle's hook, retracting the needle to remove the needle from the adjacent tissue to leave the suture loop extending through such tissue, repositioning the apparatus and extending the needle to capture at its hook the loop of suture material along another side of the tissue to be sewn, retracting the needle into the shaft with the loop of suture material captured in its hook, removing the apparatus while drawing one end of the loop of suture through the tissue to locate the loop of suture material around the tissue to be sewn, securing closed the ends of the loop of suture material, such as with a knot or crimped sleeve, and trimming the free ends of the suture extended from the secured closed tissue.

The apparatus and method are especially suitable for laproscopic procedures where the elongated shaft of the apparatus may be located to the site of the tissue to be operated upon. For example, the apparatus may be used during laproscopic prostatectomy to ligate tissue where the tissue sewn closed represents the dorsal vein complex of the penis in front of the urethra of the male patient. However, the tissue may represent any other tissue requiring suturing during surgery, or may be used in other surgical applications as a suture applying instrument tissue apart from a ligation procedure, such as wound closure.

BRIEF DESCRIPTION OF THE DRAWINGS

The foregoing objects, features and advantages of the invention will become more apparent from a reading of the following description in connection with the accompanying drawings, in which.

DETAILED DESCRIPTION OF THE INVENTION

Figure 1:
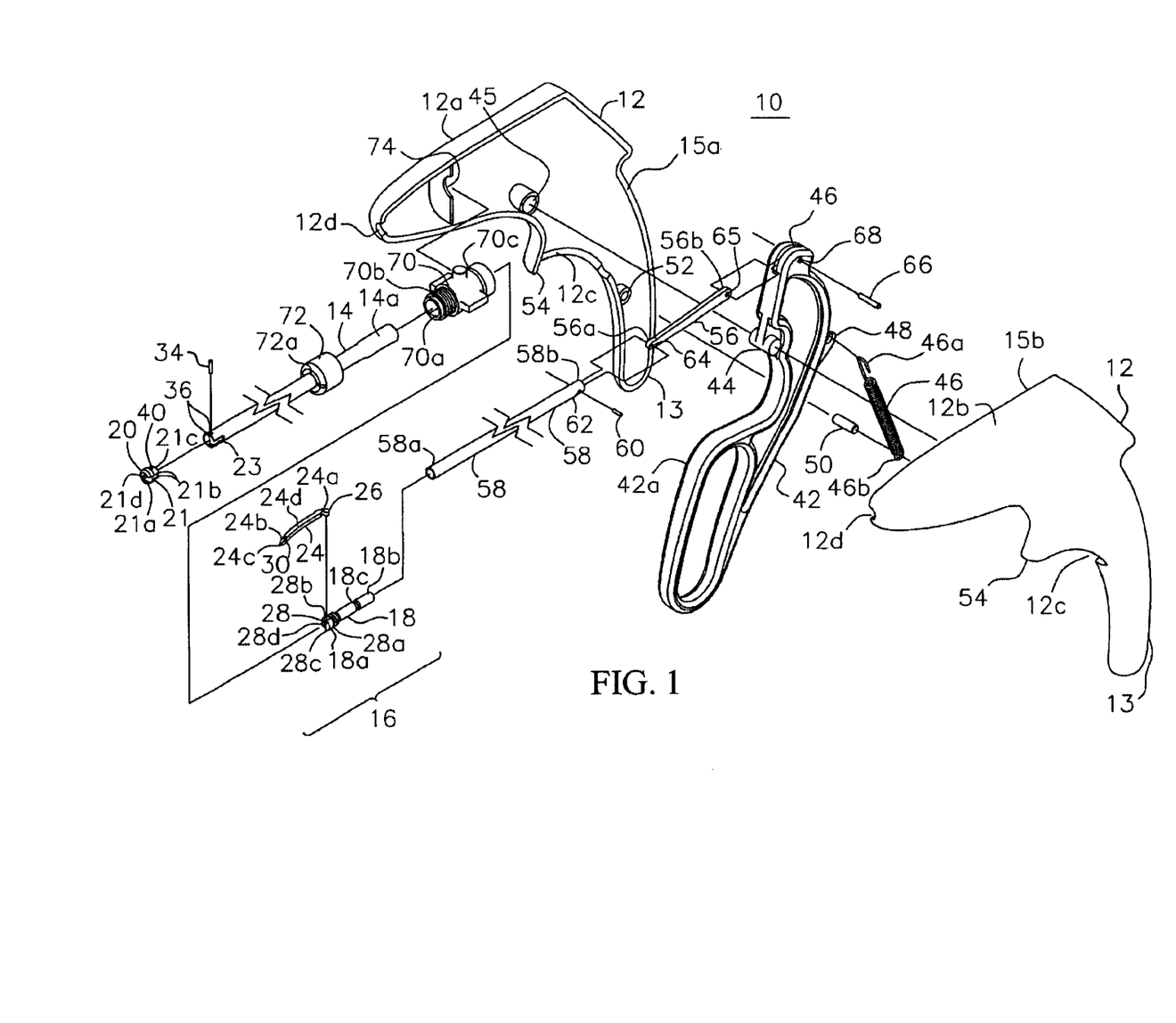
FIG. 1 is an exploded perspective view of the apparatus in accordance with the present invention.
Figures 1A, 1B:
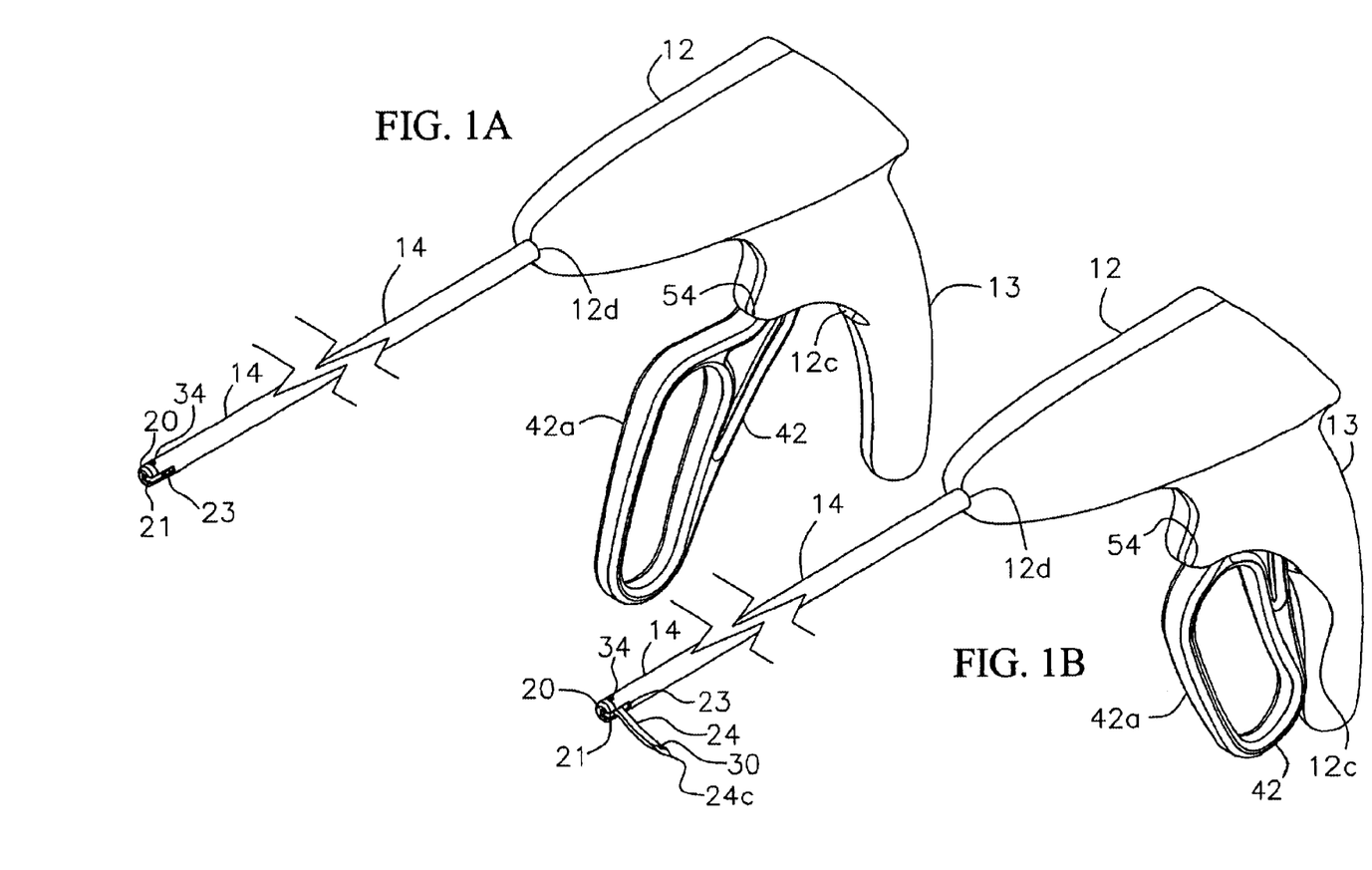
FIGS. 1A and 1B are perspective views of the apparatus of FIG. 1 showing the needle retracted and extended, respectively, from the distal end of the apparatus.
Figures 2A, 2B, 3A, 3B:
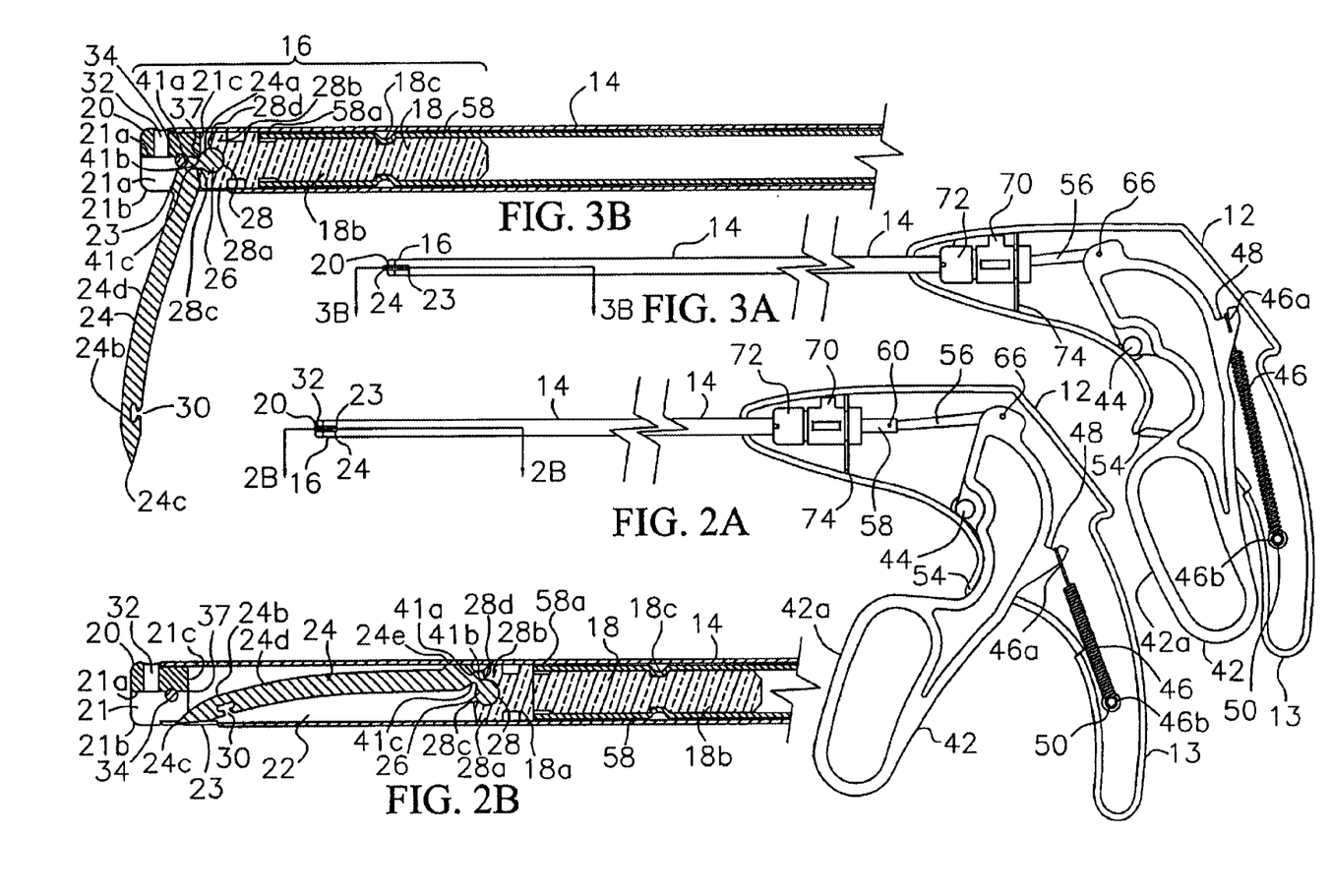
FIG. 2A is a cross-sectional view along the length of the apparatus of FIG. 1A.
FIG. 2B is a cross-sectional view along lines 2B—2B of FIG. 2A.
FIG. 3A is a cross-sectional view along the length of the apparatus of FIG. 1B.
FIG. 3B is a cross-sectional view along lines 3B—3B of FIG. 3A.

Referring to FIGS. 1, 1A, 1B, 2A, 2B, 3A, and 3B, the apparatus 10 has a housing 12 and a hollow shaft 14 extending from the housing to the shaft's distal end 16. The housing is an assembly of two sides or halves 12a and 12b. The shaft 14 may be a tube or other elongated member being cylindrical in cross-section. In the shaft at the distal end 16 is a driver member 18 disposed opposite a fixed member or cap 20 received in shaft 14. The driver member 18 is movable with respect to the cap 20 along the shaft 14. The interior surface of the shaft 14 between the driver member 18 and the cap 20 forms a cavity 22 (FIG. 2B). The cap 20 has a slot 21 having a bottom surface 21*a* and two walls 21*b* which extend from top surface 21*d* to an opening 23 and cavity 22 in the shaft. The back surface 21*c* of cap 20 and bottom surface 21*a* of the slot meet to form a ledge or step 37 (FIGS. 2B and 3B). A needle 24 is provided having one end 24*a* forming a curved member or shaft 26 which is pivotably mounted for rotation in a socket 28 at one end 18*a* of driver member 18. At the other end 24*b* of the needle 24 is a hook (or T-shaped slot) 30 near the needle's tip 24*c* capable of retaining a loop of suture material. When in a retracted position, the needle 24 lies within cavity 22 (FIG. 2B). The needle is shaped with a curvature towards the opening 23 in the shaft 14. As shown in FIGS. 2B and 3B, a hole 32 in the cap extends to slot 21 through which can extend the free ends of the loop of suture material captured in hook 30. A guide member or pin 34 is provided in the slot 21 through two openings 36 in the sides of the shaft 14 and through a hole 40 of the cap which extends through slot 21, when the cap 20 is received and forms a part of the distal end 16 of shaft 14. Socket 28 has two walls 28*a* and 28*b* which extend to form tapered fingers 28*c* and 28*d*, respectively. Needle 24 at its end 24*a* has multiple notches or grooves 41*a*, 41*b*, and 41*c*.

When the driver member 18 moves forward with the needle 24 from its retracted position in shaft 14, as shown in FIGS. 3A and 3B, the needle 24 at its surface 24*d* abuts and slides along one, or both, edge 37 or pin 34, driving the end 24*b* of the needle 24 through slot 21 of cap 30 as the curved member 26 of the needle rotates in socket 28 of the drive member 18, allowing the needle to exit out of opening 23 and slot 21, until fully actuated to an approximately 90 degree angle with respect to the shaft 14. When the needle 24 is fully actuated, pin 34 is received in notch 41*a* near the end 24*a* of the needle 24, cap ledge 37 is received in notch 41*b*, and finger 28*c* is received in notch 41*c* of needle 24, thereby releasibly locking the position of the needle 24, as shown in FIGS. 1B, 3A and 3B. The cavity 22 in shaft 14 formally holding needle 24 is no longer present (or reduced in size) when the needle is fully driven forward. When the driver member 18 moves backwards, the pin 34, ledge 37, and finger 28*c* are removed from their respective notches of needle 24, releasing the needle 24, and the needle again at its surface 24*d* abuts and slides along one, or both, edge 37 or pin 34, as it pivots backwards in socket 28 through opening 23 and slot 21 into shaft 14, as shown in FIGS. 1A, 2A and 2B. When in its fully retracted position, surface 24*e* of the needle 24 may abut the interior surface of shaft 14, and finger 28*d* is received in notch 41*b* of the needle. The curvature of the needle 24 allows the needle as its slides forward along pin 24 or cap ledge 37 to pivot in the direction of slot 21 and opening 23. Slot 21 with opening 23 provides a slotted opening at distal end 16.

The drive mechanism to extend and retract the needle 24 includes lever 42, drive link member 56, drive tube 58, and driver member 18 to move the driver member linearly at the distal end of the shaft. The driver member 18 has a cylindrical shaft 18*b* extending from its end 18*a*. The cylindrical shaft 18*b* is received into one end 58*a* of the drive tube 58 and attached thereto, such as staked, i.e., deformed, such as by a press, at one or more locations, into an annular groove 18*c* about cylindrical shaft 18*b*. The drive tube 58 has an outer diameter less than the inner diameter of shaft 14 such that the drive tube is slidable in shaft 14. The diameter of shaft 18*b* of the drive member is such that it is received in can be received in drive tube 58, with the end 18*a* of the driver member being of slightly larger in diameter but less than the inner diameter of shaft 14, such that end 18*a* is also slidable in the shaft 14 along with drive tube 58. End 56*a* of the drive link member 56 is received into the drive tube 58 at its end 58*b*. A pin 60 couples the drive tube 58 to the drive link member 56 through two holes 62 in the sides of the drive tube 58 and through a hole 64 at end 56*a* of the drive link member 56.

The drive link member 56 is coupled to the lever 42 by a pin 66 through a hole 68 extending through a slot 46 in the lever and a hole 65 at end 56*b* of the drive link member 56. The lever 42 has a shaft 44 molded as part of the lever having ends received into holes 45 in each of the sides 12*a* and 12*b*, respectively, of housing 12 upon which the lever is pivotally mounted in the housing. The lever 42 has a portion 42*a* which extends through an opening 12*c* of the housing 12 to enable pivotal movement about shaft 44. An extension spring 46 is provided which hooks at one end 46*a* in a notch 48 of the lever 42 and is wound at the other end 46*b* around a pin 50 located in holes 52 in the sides 12*a* and 12*b* of housing 12, such that the lever 42 is spring biased to retain the lever normally in a forward position. The body of housing 12 has a front portion 54 providing a stop that limits the pivotal forward movement of the lever 42, as best shown in FIGS. 1A and 2A. The assembly of the needle 24, driver member 18, drive tube 58, and drive link member 56 are received through the shaft 14.

To mount shaft 14 to housing 12, the shaft 14 has an end 14*a* which is D-shaped and registered into a corresponding shaped opening 70*a* of an adapter 70, and a threaded nut 72 having an opening 72*a* which extends over shaft 14 and screws onto the threaded end 70*b* of the adapter 70 to secure shaft 14 to adapter 70. The drive tube 58 and drive link member 56 are movable through the shaft 14 via opening 70*a* extending through the adapter 70. An internal flange 74 in each housing half 12*a* and 12*b* supports the adapter along an annular groove 70*c* of the adapter 70. The shaft 14 extends from housing 12 via an opening 12*d* in the housing.

The two halves 12*a* and 12*b* of housing 12 may be made of molded plastic which mate along edges 15*a* and 15*b*, respectively. The housing 12 may have a body shaped like a pistol having a handle portion 13. The two halves 12*a* and 12*b* are attached to each other along their edges 15*a* and 15*b*, such as by adhesive or sonic welding, with the assembled distal end 14 of shaft 14 and drive mechanism of the components 18, 56, and 58 extending therethrough to lever 42. The shaft 14 may be, for example, of length and diameter enabling the shaft to be insertable into a patient's body for laproscopic procedures. For example, the shaft may be about 12 inches in length and have an outer diameter of about 5 mm. The cap 20, driver member 18, drive tube 58, and needle 24 may be made of stainless steel or other biocompatible material, while adapter 70, nut 72, and drive link member 56 may be made of metal or preferably molded plastic.

In operation, an operator by pulling the lever 42 back towards the handle portion 13 of housing 12, rotates the lever 42 about shaft 44, thereby pushing forward the drive link member 56 as it rotates along pin 66, and the drive tube 58 coupled to the drive link member 56 at pin 60, such that driver member 18 at end 58*a* of the drive tube 58 is driven forward and pivots the needle 24 rotationally mounted thereto to extend from the distal end 16 until fully actuated, as described earlier. When the operator releases the lever 42 allowing it to move forward, the drive member 18, drive tube 58, and drive link member 56, move in the opposite direction to retract the needle 24 into the distal end 16.

Figure 4A:
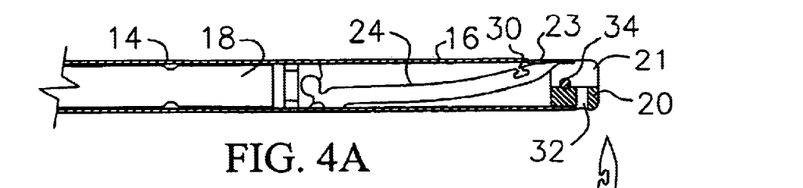
FIGS. 4A–4E illustrate the loading of a loop of suture material in the apparatus of the present invention.
Figure 4B:
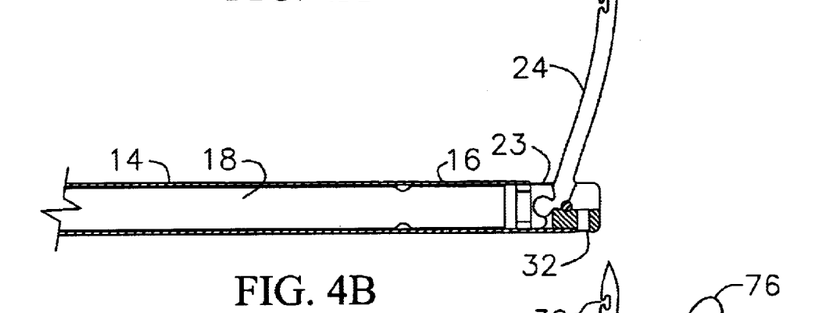
Figures 4C, 4D:
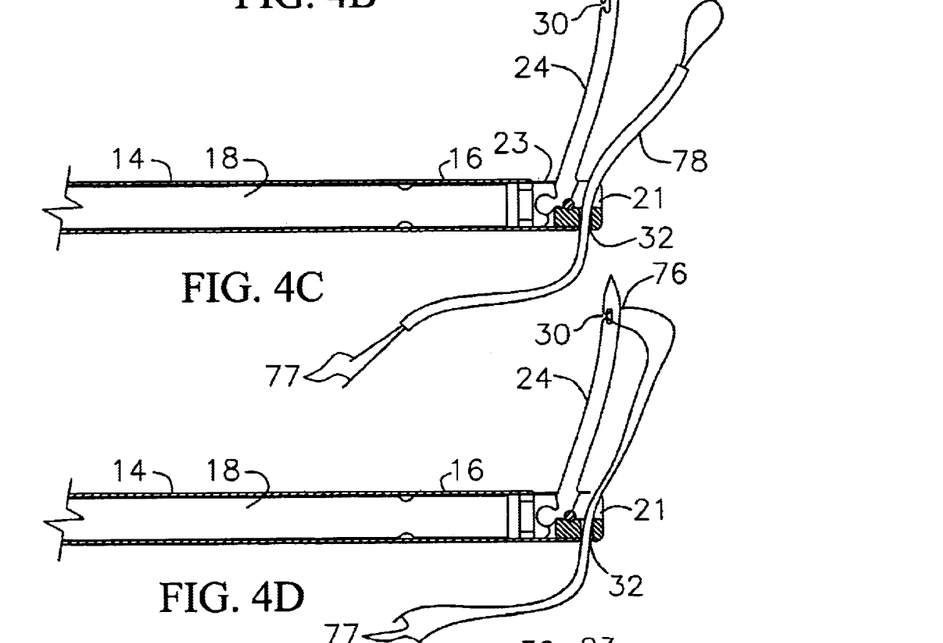
Figure 4E:
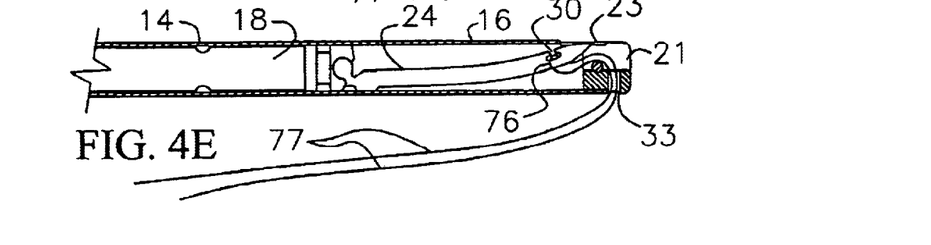

Referring to FIGS. 4A–4E, the process of loading suture material or thread in apparatus 10 is shown. FIG. 4A shows the distal end 16 with the needle 24 in its retracted position prior to suture loading. The needle is extended from distal end 16 (FIG. 4B), and then a loop of suture 76 having two free ends 77 extending through a flexible tube 78 is threaded through hole 32, slot 21 and opening 23 of the distal end 16 (FIG. 4C). The loop of suture 76 is then located in hook 30 and the flexible tube 78 is removed (FIG. 4D). The needle 24 is then retracted into the distal end 16 while pulling the ends 77 of the loop suture 76 through hole 23. Loading of the apparatus 10 is complete (FIG. 4E). The free ends 77 of the suture loop may be held by the operator of the apparatus from housing 12 along the shaft 14. Flexible tube 78 may be made, for example, of plastic.

Figure 5A:
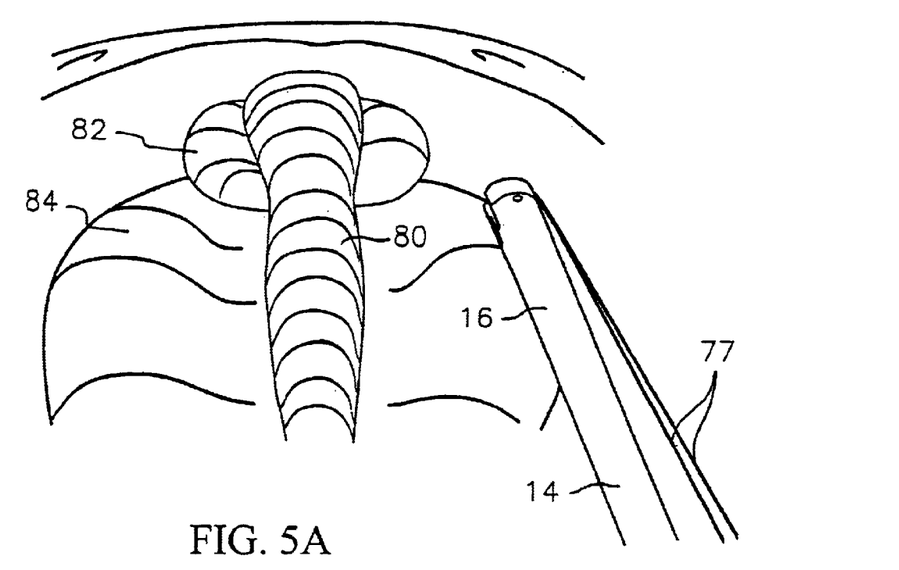
FIGS. 5A–5I illustrate an example of the method of using the apparatus to ligate the dorsal vein complex of the penis which may be part of a laproscopic prostatecomy.
Figure 5B:
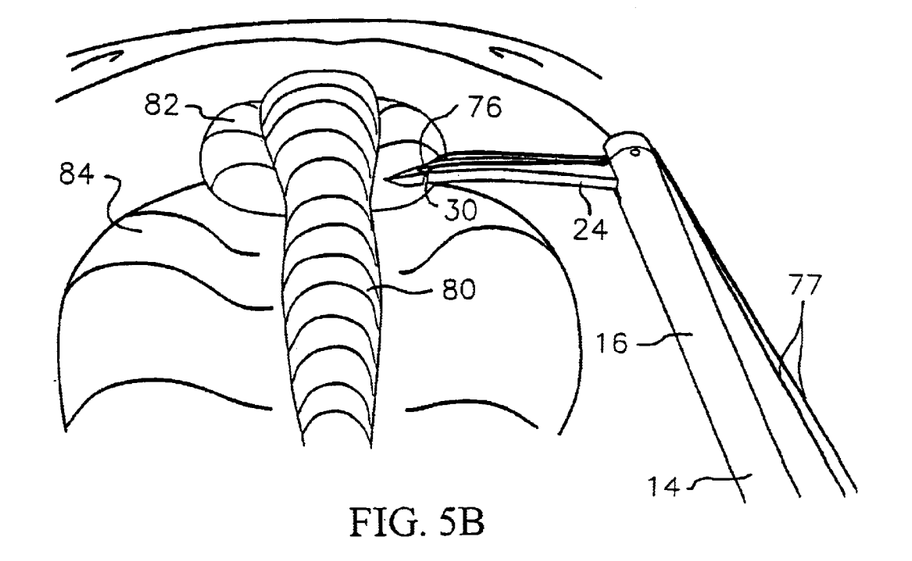
Figure 5C:
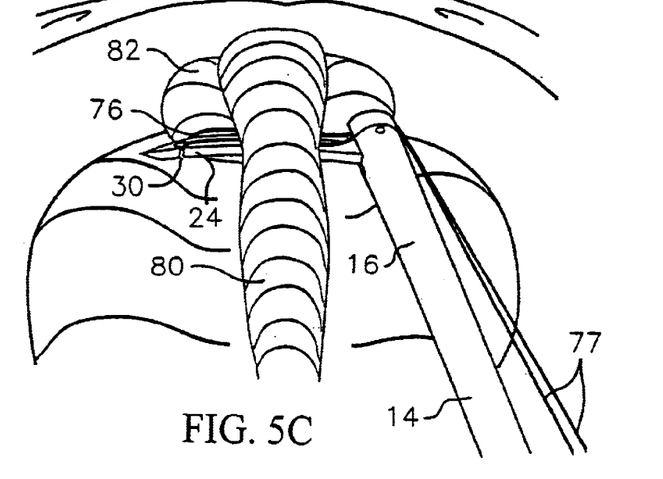
Figure 5D:
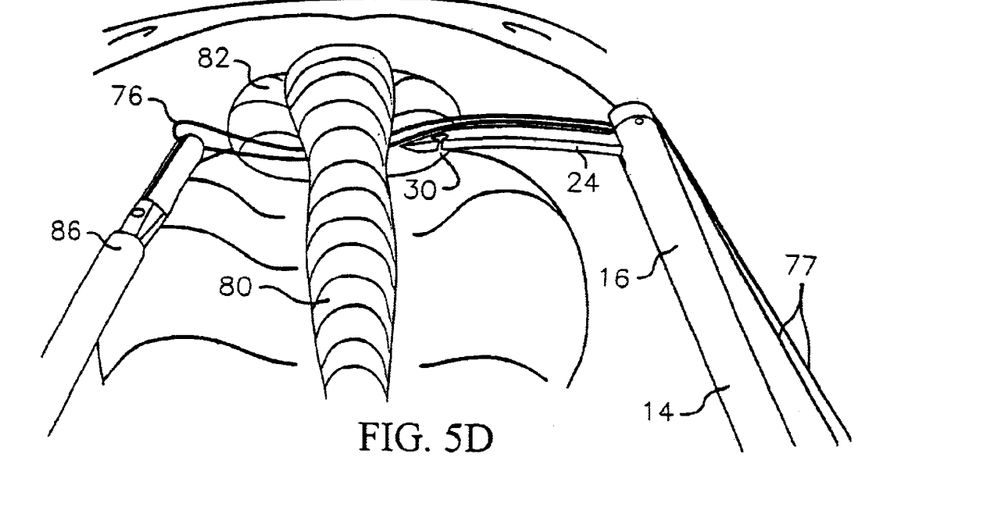
Figure 5E:
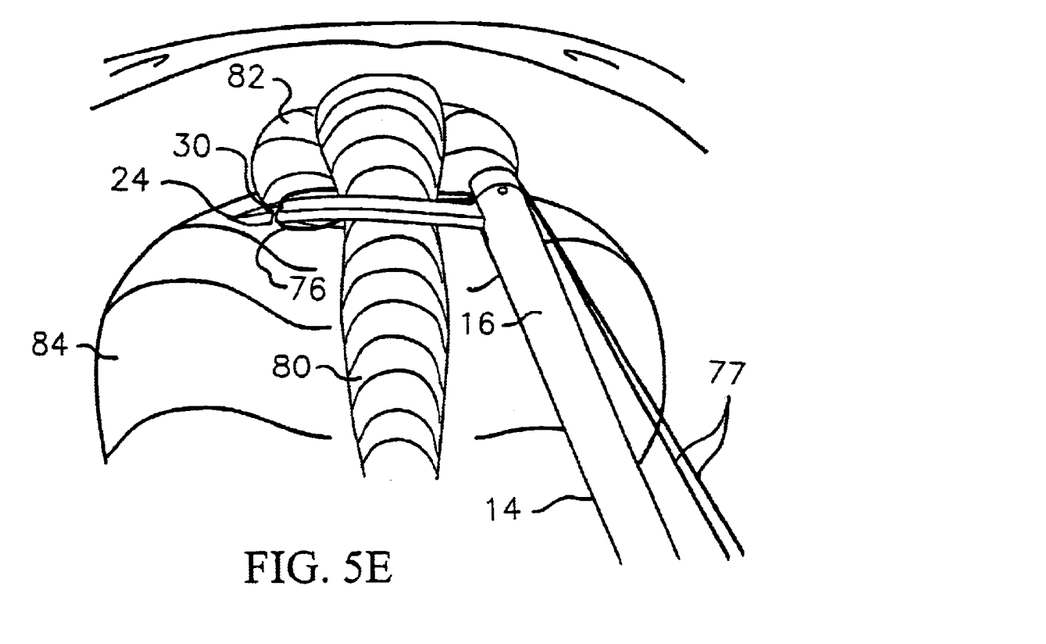
Figure 5F:
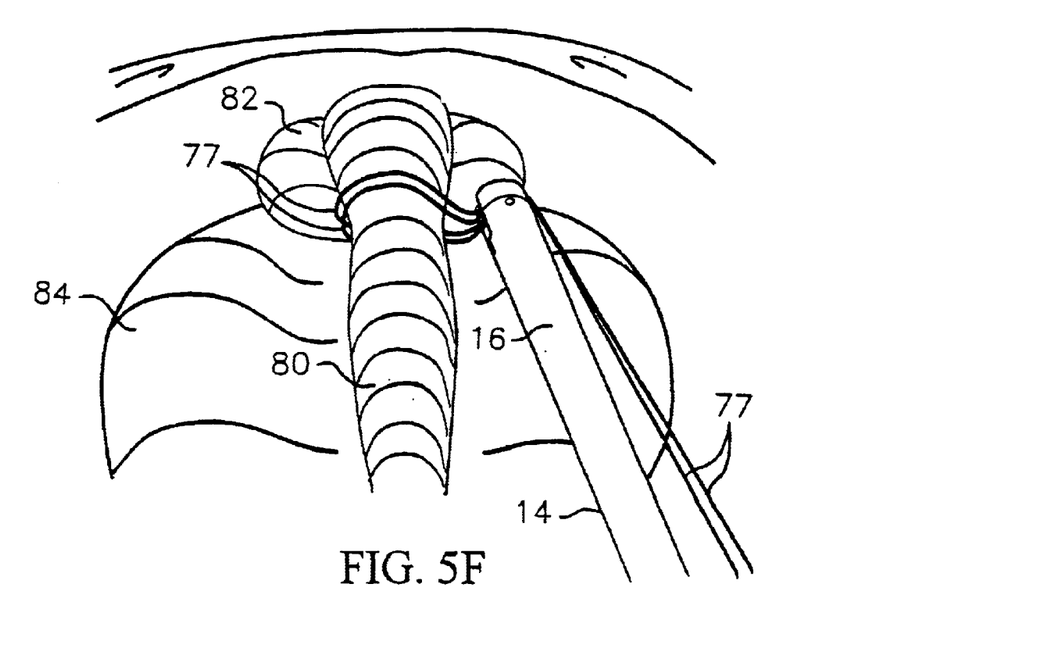
Figure 5G:
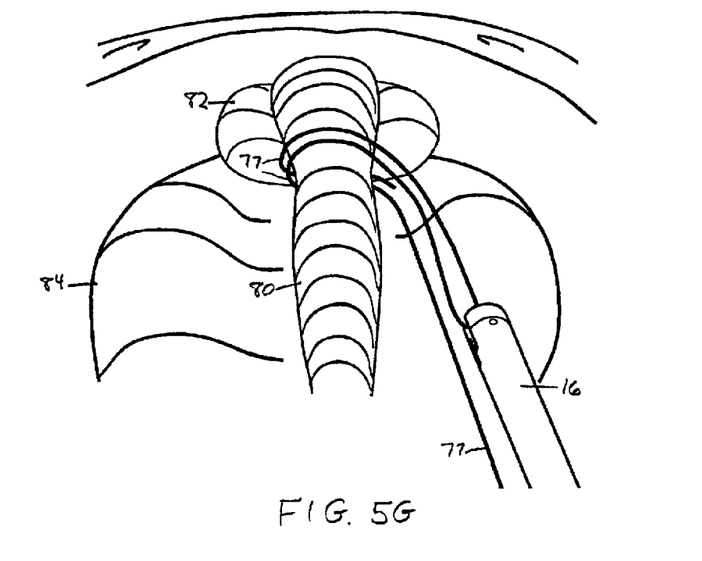
Figure 5H:
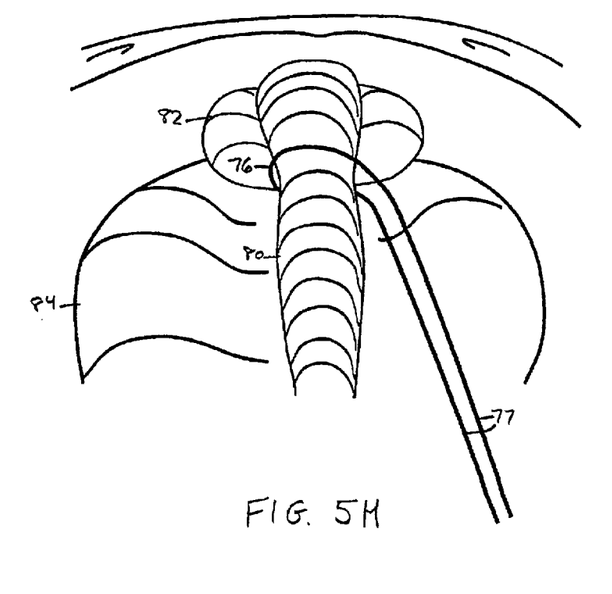
Figure 5I:
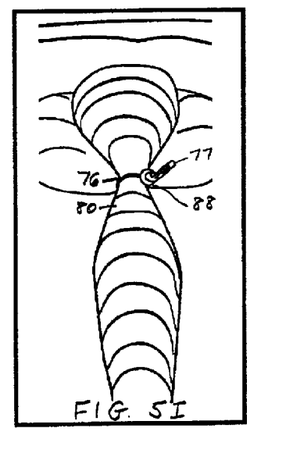

Referring to FIGS. 5A–5H, the method of using the apparatus 10 to sew tissue is shown so as to ligate tissue. For purposes of illustration, the tissue 80 to be ligated is the dorsal vein complex of the penis, but the apparatus may be used with other tissue. The apparatus is particularly useful as a laproscopic surgical instrument which may be inserted into a patient through a small incision in the patient's body with or without a cannula, as typical of laproscopic procedures. The views shown in these figures may be typical of that provided by a laproscopic camera of the male pelvic region, such as during a prostatecomy procedure. As shown in FIG. 5A, the distal end 16 of the apparatus 10 with loaded suture is first presented to the tissue 80 to be ligated, with the free ends 77 of the suture loop 76 extending form the distal end 16 along the shaft 14. The operator, such as a surgeon, pulls the lever 24 to deploy the needle 24 from distal end 16 (FIG. 5B) to extend toward tissue adjacent the tissue 80 to be ligated, i.e., in the direction between the dorsal vein complex and the urethra 82. The needle 24 with the suture loop 76 is inserted through the tissue between the posterior dorsal vein complex 80 and anterior urethra 82 (FIG. 5C). Next, the suture loop 76 is released and held on exit side of tissue site by a grasper instrument or laproscopic forceps 86, and the apparatus 10 moved to pull back the needle 24 through the tissue leaving the suture loop extending therethrough (FIG. 5D). The extended needle 24 is repositioned on the other or opposite side of tissue 80 by moving apparatus 10, and the suture loop 76 reloaded or captured into needle hook 30 above the tissue 80 (FIG. 5E). Needle 24 and suture loop 76 are then retracted back into distal end 16 (FIG. 5F). While the surgeon holds only one of the free ends 77 of the suture, the apparatus 10 is pulled away from the tissue 80 (FIG. 5G) and the suture is drawn through the tissue leaving the suture loop 76 around the dorsal vein complex 80 (FIG. 5H). The mid section of the suture is thus behind the tissue 80 and the suture ends on opposite sides of the tissue 80. The loop is secured closed at 88 to ligate tissue 80, and suture free ends 77 or tails extending from the secured closed loop of suture are trimmed (FIG. 5I). Various means 88 for securing closed the free ends of the suture may be used, such as with a knot placed by a surgeon, or using a suture securing instrument, such as the Ti-KNOT® TK•5™ manufactured by LaserSurge, Inc. of Rochester, N.Y.

The apparatus 10 may be used to apply suture through tissue in the body of a patient for other procedures than ligation, such as to secure a wound closed. For example, the apparatus 10 with the needle 24 extended from the distal end 16 is passed through a first location about a wound in tissue, and then the loop of suture removed from the needle hook 30. The apparatus 10 is then repositioned and the loop of suture recaptured. The needle 24 then is passed through a second location about the wound, and the loop again removed from the needle's hook 30. The extended needle 24 is again repositioned and the loop of suture is captured on the needle's hook 30 and needle 24 and suture loop retracted into the distal end. Alternatively, a single pass of needle 24 through two locations in the tissue about the wound may be performed, rather than two passes of the needle. The apparatus 10 is then pulled away from the tissue, and the suture drawn through while one end of the suture is held, leaving the loop of suture through the first and second locations in tissue about the wound. The loop may then be secured closed and free ends trimmed, as described earlier.

The apparatus 10 may also be used as a sewing instrument to apply multiple stitches in tissue by inserting the needle when extended from the distal end 16 through tissue where for each pass through the tissue with the needle: the loop of suture is removed from the needle, the needle removed from the tissue, and then the needle is reloaded within the patient with the loop of suture for the next pass through the tissue.

Although one loop of suture material is described, multiple loops of suture material may be loaded simultaneously, as described earlier, into the apparatus, and used to apply multiple loops of suture about tissue in the same manner as applying a single loop. These multiple loops of suture material may be of the same or of different colors.

From the foregoing description, it will be apparent that an improved apparatus and method for sewing tissue has been provided. Variations and modifications in the herein described apparatus and method in accordance with the invention will undoubtedly suggest themselves to those skilled in the art. Accordingly, the foregoing description should be taken as illustrative and not in a limiting sense.

What is claimed is:

1. An apparatus for applying suture material through tissue comprising:
   a housing;
   a shaft having a distal end which extends from said housing to said distal end;
   said distal end having a fixed member disposed opposite a driver member, and a slotted opening;
   means for driving said driver member to move forward and backward with respect to said fixed member; and
   a needle having one end pivotably mounted to said driver member to pivot and extend through said slotted opening when said driver member is moved forward, and another end having a slot for suture material.

2. The apparatus according to claim 1 wherein said distal end of said shaft has a hole through which the suture material is extendable to said slot of said needle.

3. The apparatus according to claim 2 wherein said suture material represents a loop of suture material received in said slot of said needle and has two free ends which extend through said hole, in which said needle is capable of locating said loop of suture material through tissue when extended through said slotted opening.

4. The apparatus according to claim 2 wherein said suture material represents a loop of suture material received in said slot of said needle and has two free ends which extend through said hole, in which said needle when extended from said distal end is capable of locating said loop of suture material through tissue, and said loop of suture material is removable from said slot of said needle while said suture material and needle are located through said tissue.

5. The apparatus according to claim 1 wherein said driving means comprises:

a lever pivotably mounted in said housing; and means for translating motion to said drive member through said shaft when said lever pivots.

6. The apparatus according to claim 5 wherein said translating means comprises a drive tube, a drive link member for linking said drive tube to said lever, and said drive tube has an open end into which said driver member is received and attached.

7. The apparatus according to claim 1 wherein said needle is curved to facilitate exiting said slotted opening.

8. The apparatus according to claim 1 further comprising a guide member located in said slotted opening to guide said needle when extending or retracting through said slotted opening.

9. The apparatus according to claim 1 wherein said needle rides along a part of said slot when extending or retracting through said slotted opening.

10. The apparatus according to claim 1 wherein said shaft represents a tube with an open end, and said fixed member represents a cap received in said open end of said shaft in which said slotted opening is provided by an opening in said tube and a slot in said cap.

11. The apparatus according to claim 1 wherein said driver member has a socket and said end of said needle pivotably mounted to said drive member is rotatable in said socket.

12. The apparatus according to claim 1 further comprising means for releasibly locking the forward position of the needle when fully extended.

13. The apparatus according to claim 1 wherein said slot of said needle is capable of holding one or more loops of suture material.

14. The apparatus according to claim 1 wherein said apparatus represents a surgical instrument for laproscopically ligating tissue.

15. A method for ligating tissue with an apparatus having a shaft and a needle extendible and retractable from said shaft, said needle having slot through which extends a loop of suture material have two free ends, said method comprising the steps of:

extending the needle from said shaft;

locating said extended needle through adjacent tissue along one side of the tissue to be ligated;

removing the loop of said suture material from said needle while said suture material and needle are located through said adjacent tissue;

removing said needle from said adjacent tissue to leave said loop of suture material extending therethrough;

positioning said needle to capture said loop of suture material along another side of the tissue to be ligated;

retracting the needle into said shaft;

pulling said suture material through said adjacent tissue to provide said loop of suture around said tissue to be ligated; and securing closed the free ends of the loop of suture material to ligate the tissue.

16. The method according to claim 15 wherein said removing step is carried out with the aid of an instrument for grasping the loop of suture material from said slot of said needle.

17. The method according to claim 15 further comprising the step of trimming the free ends near the secured closed loop of suture material.

18. The method according to claim 15 wherein said loop of suture material represents one or more loops of suture material.

19. A method for sewing tissue with an instrument having a shaft and a needle extendible and retractable from a distal end of said shaft, said method comprising the steps of:

loading a loop of suture material through a slot of said needle;

placing said distal end of shaft near the tissue to be sewn;

extending said needle from said distal end;

passing said extended needle and loop of suture material through tissue;

removing said loop of suture material from said needle;

removing the needle from said tissue to leave the loop of suture extending therethrough; and positioning the extended needle to recapture said loop of suture material in said needle slot.

20. The method according to claim 19 further comprising the steps of:

retracting the needle with the recaptured loop of suture material into said shaft;

pulling the loop of suture material through said tissue as the instrument is removed to locate the loop about the tissue; and securing the loop of suture closed.

21. The method according to claim 20 further comprising the step of trimming the free ends near the secured closed loop of suture material.

22. The method according to claim 19 wherein said loop of suture material is passed through the tissue at a first location, and said method further comprises the step of passing the needle with the recaptured loop of suture material through a second location in the tissue.

23. The method according to claim 22 further comprising the steps of:

pulling the loop of suture material through the tissue as the instrument is removed to draw the loop of the suture material through said first and second locations of the tissue; and securing the loop of suture material closed.

24. The method according to claim 23 wherein said first and second locations are about a wound in the tissue.

25. The method according to claim 23 further comprising the step of trimming free ends near the secured closed loop of suture material.

26. The method according to claim 19 wherein said needle passes through two locations in the tissue.

* * * * *